US008815945B2

(12) United States Patent
Nagai et al.

(10) Patent No.: US 8,815,945 B2
(45) Date of Patent: *Aug. 26, 2014

(54) **USE OF *BIS* [THIOHYDRAZIDE AMIDE] COMPOUNDS SUCH AS ELESCLOMOL FOR TREATING CANCERS**

(76) Inventors: Masazumi Nagai, Lexington, MA (US); Ronald K. Blackman, Brookline, MA (US); Patricia E. Rao, Acton, MA (US); Yumiko Wada, Tokyo (JP); Keizo Koya, Brookline, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/642,275

(22) PCT Filed: Apr. 20, 2011

(86) PCT No.: PCT/US2011/033256
§ 371 (c)(1),
(2), (4) Date: Mar. 1, 2013

(87) PCT Pub. No.: WO2011/133673
PCT Pub. Date: Oct. 27, 2011

(65) Prior Publication Data
US 2013/0150440 A1 Jun. 13, 2013

Related U.S. Application Data

(60) Provisional application No. 61/342,822, filed on Apr. 20, 2010.

(51) Int. Cl.
*A61K 45/06* (2006.01)
*A61K 31/19* (2006.01)
*A61K 31/337* (2006.01)

(52) U.S. Cl.
USPC ........................................................ 514/500

(58) Field of Classification Search
USPC ........................................................ 514/500
See application file for complete search history.

(56) References Cited

U.S. PATENT DOCUMENTS

| | | | |
|---|---|---|---|
| 6,762,204 B2 | 7/2004 | Koya et al. |
| 6,800,660 B2 | 10/2004 | Koya et al. |
| 6,825,235 B2 | 11/2004 | Chen et al. |
| 6,924,312 B2 | 8/2005 | Koya et al. |
| 7,001,923 B2 | 2/2006 | Koya et al. |
| 7,037,940 B2 | 5/2006 | Koya et al. |
| 7,074,952 B2 | 7/2006 | Chen et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 7,579,503 B2 | 8/2009 | Koya et al. |
| 7,645,904 B2 | 1/2010 | Chen et al. |
| 7,652,168 B2 | 1/2010 | Chen et al. |
| 7,671,092 B2 | 3/2010 | Koya et al. |
| 7,678,832 B2 | 3/2010 | Lunsmann et al. |
| 7,709,683 B2 | 5/2010 | Chen et al. |
| 7,750,042 B2 | 7/2010 | Koya et al. |
| 7,763,658 B2 | 7/2010 | Koya et al. |
| 7,795,313 B2 | 9/2010 | Koya et al. |
| 2005/0043250 A1* | 2/2005 | Lampidis et al. ............... 514/23 |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2007/0088057 A1 | 4/2007 | Lunsmann et al. |
| 2008/0118562 A1 | 5/2008 | Koya |
| 2008/0119440 A1 | 5/2008 | Koya |
| 2008/0176828 A1 | 7/2008 | Williams et al. |
| 2008/0226588 A1 | 9/2008 | McLeod |
| 2009/0023736 A1 | 1/2009 | Koya et al. |
| 2009/0042991 A1 | 2/2009 | Barsoum et al. |
| 2009/0093538 A1 | 4/2009 | Bertin et al. |
| 2009/0137682 A1 | 5/2009 | Dahl |
| 2010/0068174 A1 | 3/2010 | Jacobson |
| 2010/0081635 A1 | 4/2010 | Chen et al. |
| 2010/0093828 A1 | 4/2010 | Koya et al. |
| 2010/0249239 A1 | 9/2010 | Lunsmann et al. |
| 2010/0280075 A1 | 11/2010 | Koya et al. |
| 2010/0324143 A1 | 12/2010 | Koya et al. |
| 2011/0098476 A1 | 4/2011 | Chen et al. |
| 2011/0196025 A1 | 8/2011 | Kostik et al. |
| 2011/0245262 A1 | 10/2011 | Sun et al. |
| 2011/0245577 A1 | 10/2011 | Koya |
| 2011/0288162 A1 | 11/2011 | Masazumi et al. |
| 2011/0294814 A1 | 12/2011 | Kowalczyk-Prezewloka et al. |
| 2011/0294877 A1 | 12/2011 | Masazumi et al. |

(Continued)

FOREIGN PATENT DOCUMENTS

WO WO 2006/009940 * 1/2006 ............. A61K 31/16
WO WO-2008/027445 A2 3/2008

(Continued)

OTHER PUBLICATIONS

Kornberg, Serum lactic dehydrogenase (LDH) levels in acute leukemia: marked elevations in lymphoblastic leukemia, Blood, 56: 351-355, 1980.*
Takatsuki et al., Clinical Diversity in Adult T-Cell Leukemia-Lymphoma, Cancer Research Suppl., 45, 4644s-4645s, 1985.*
Thornburg et al., Targeting Aspartate Aminotransferase in Breast Cancer, Breast Cancer Res.;10(5):1-17, 2008.*
Huijgen et al., The Clinical Value of Lactate Dehydrogenase in Serum: A Quantitative Review, Eur J Clin Chem Clin Biochem, 35(8):569-579, 1997.*
El-Asmy et al., Structural studies on cadmium(II), cobalt(II), copper(II), nickel(II) and zinc(II) complexes of 1-malonyl-bis(4-phenylthiosemicarbazide, Transition Met. Chem., 15:12-15, 1990.*
Anonymous: "Synta Pharmaceuticals Announces Updated Elesclomol SYMMETRYSM Data Presented at Melanoma XIII", Medicalnewstoday.com Release, Oct. 14, 2009.

(Continued)

*Primary Examiner* — Jeffrey S. Lundgren
*Assistant Examiner* — Zenab Olabowale
(74) *Attorney, Agent, or Firm* — McCarter & English, LLP; Steven G. Davis

(57) ABSTRACT

Improved cancer treatments with bis[thiohydrazide amide] compounds such as elesclomol, in particular for identifying patient populations that would benefit from such treatments.

16 Claims, 14 Drawing Sheets

(56) References Cited

U.S. PATENT DOCUMENTS

| | | |
|---|---|---|
| 2011/0294895 A1 | 12/2011 | Lunsmann et al. |
| 2012/0035266 A1 | 2/2012 | Koya et al. |
| 2012/0065206 A1 | 3/2012 | Jiang et al. |
| 2012/0065235 A1 | 3/2012 | Sun et al. |

FOREIGN PATENT DOCUMENTS

| | | |
|---|---|---|
| WO | WO-2009/079338 A1 | 6/2009 |
| WO | WO-2010/048293 A1 | 4/2010 |
| WO | WO-2010/002465 A2 | 5/2010 |

OTHER PUBLICATIONS

Nagai, M. et al., Abstract #C11: The Oxidative Stress Inducer Elesclomol Requires Copper Chelation for its Anticancer Activity, AACR-NC1-EORTC *Molecular Targets and Cancer Therapeutics*, Nov. 15, 2009, XP002641815.

Nagai, M. et al., Abstract 4545: Anticancer Activity of Elesclomol Correlates with Low LDH Levels and Active Mitochondrial Respiration, *Cancer Research*, vol. 70, No. 8 Supplement, Apr. 15, 2010, XP055000610.

Zhou, Ming et al. "Warburg Effect in Chemosensitivity: Targeting Lactate Dehydrogenase-A re-Sensitises Taxol-Resistant Cancer Cells to Taxol", *Molecular Cancer*, 2010, 9:33.

\* cited by examiner

USE OF BIS [THIOHYDRAZIDE AMIDE] COMPOUNDS SUCH AS ELESCLOMOL FOR TREATING CANCERS

CROSS-REFERENCE TO RELATED APPLICATIONS

This application is a 35 U.S.C. §371 national stage filing of International Application No. PCT/US2011/033256, filed Apr. 20, 2011, which claims priority to U.S. Provisional Application No. 61/342,822, filed Apr. 20, 2010. The entire contents of these applications are explicitly incorporated herein by reference.

FIELD OF THE INVENTION

The present disclosure relates to improved methods for treating cancer with bis[thiohydrazide amide] compounds such as elesclomol, in particular for identifying patient populations that would benefit from such treatment methods.

BACKGROUND OF THE INVENTION

Elesclomol (see, e.g., U.S. Pat. Nos. 6,800,660; 6,762,204; 7,037,940; 7,001,923; and 6,924,312) is a first-in-class investigational drug that induces apoptosis in cancer cells through the elevation of reactive oxygen species (ROS). Elesclomol selectively chelates copper and generates ROS via reduction of Cu(II) to Cu(I). Elesclomol has been shown to have potent anti-cancer activity, e.g., in combination with paclitaxel. However, additional insight, into which patients or patient population would benefit from bis[thiohydrazide amide] compounds such as elesclomol, would enable health care professionals to more effectively treat patients in need.

SUMMARY OF THE INVENTION

The present disclosure is directed towards methods of treating cancer in a patient at risk of having cancer cells with elevated lactate dehydrogenase levels. These methods include administering to the subject an effective amount of a bis[thiohydrazide amide] compound, such as:

(I)

or a deprotonated form thereof complexed to a transition metal cation; or a compound represented by the following structural formula:

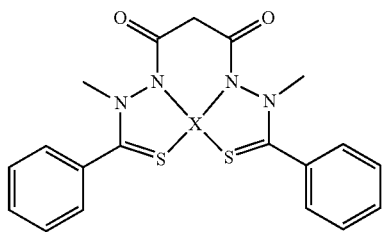

(II)

wherein X is a transition metal cation with a +2 charge, e.g., $Ni^{2+}$, $Cu^{2+}$, $Co^{2+}$, $Fe^{2+}$, $Zn^{2+}$, $Pt^{2+}$ or $Pd^{2+}$; advantageously X is $Cu^{2+}$; and an effective amount of an LDH inhibitor is administered to the patient.

The present disclosure is directed towards methods of treating cancer in a patient determined to have normal to low lactate dehydrogenase levels. These methods include administering to the subject an effective amount of a bis[thiohydrazide amide] compound, such as:

(I)

or a deprotonated form thereof complexed to a transition metal cation; or a compound represented by the following structural formula:

(II)

wherein X is a transition metal cation with a +2 charge, e.g., $Ni^{2+}$, $Cu^{2+}$, $Co^{2+}$, $Fe^{2+}$, $Zn^{2+}$, $Pt^{2+}$ or $Pd^{2+}$; advantageously X is $Cu^{2+}$.

Yet another method disclosed herein includes treating cancer in a patient determined to have elevated lactate dehydrogenase levels, wherein an effective amount of a bis[thiohydrazide amide] compound such as:

(I)

or a deprotonated form thereof complexed to a transition metal cation; or a compound represented by the following structural formula:

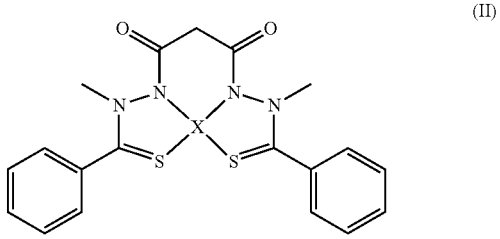

(II)

wherein X is a transition metal cation with a +2 charge; and an effective amount of an LDH inhibitor is administered to the patient.

In an embodiment, the LDH inhibitor is oxamic acid or a salt thereof. The LDH inhibitor may inhibit LDH-A.

In another embodiment, a method of treating a patient for cancer includes determining the lactate dehydrogenase level in the patient; comparing the lactate dehydrogenase level to an upper limit of normal value (ULN); determining whether the lactate dehydrogenase level is over the ULN; and, administering to the subject an effective amount of a bis[thiohydrazide amide] compound such as:

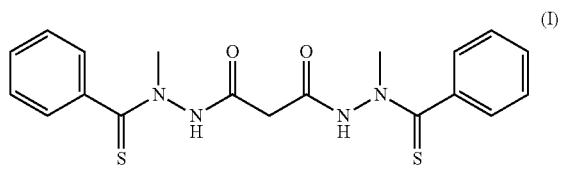 [SMILES: CN(NC(=O)CC(=O)NN(C)C(=S)c1ccccc1)C(=S)c1ccccc1]

(I)

or a deprotonated form thereof complexed to a transition metal cation; or a compound represented by the following structural formula:

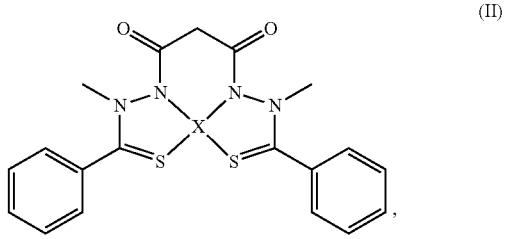

(II)

wherein X is a transition metal cation with a +2 charge; provided that if the lactate dehydrogenase level is above the ULN, an effective amount of an LDH inhibitor is also administered to the patient.

In another embodiment, a method of treating a patient for cancer includes determining the lactate dehydrogenase level in the patient; comparing the lactate dehydrogenase level to an upper limit of normal value (ULN); and, if the lactate dehydrogenase level is below the ULN (the patient has normal or low lactate dehydrogenase levels), administering to the subject an effective amount of a bis[thiohydrazide amide] represented by Formula (I) or a deprotonated form thereof complexed to a transition metal cation; or a compound represented by Formula (II). If the lactate dehydrogenase level is above the ULN (is elevated), the patient is not administered a bis[thiohydrazide amide] represented by Formula (I) or a deprotonated form thereof complexed to a transition metal cation; or a compound represented by Formula (II), but is rather administered an alternative anti-cancer therapy that does not include administration of these compounds. For patients being administered compounds of Formula (I) or (II), the lactate dehrogenase levels can be monitored during treatment. Optionally, the treatment with these compounds can be terminated if lactate dehyrogenase levels become elevated or switched to an alternate anti-cancer therapy. For example, monitoring can be weekly or monthly.

The cancer to be treated may be, e.g., renal cancer, skin cancer, bone marrow cancer, blood cell cancer (e.g., leukemia, lymphoma or myeloma), prostate cancer, ovarian cancer, or breast cancer.

Other aspects or embodiments of the invention will be disclosed in further detail later in this patent specification.

DETAILED DESCRIPTION OF THE INVENTION

Figure 1:
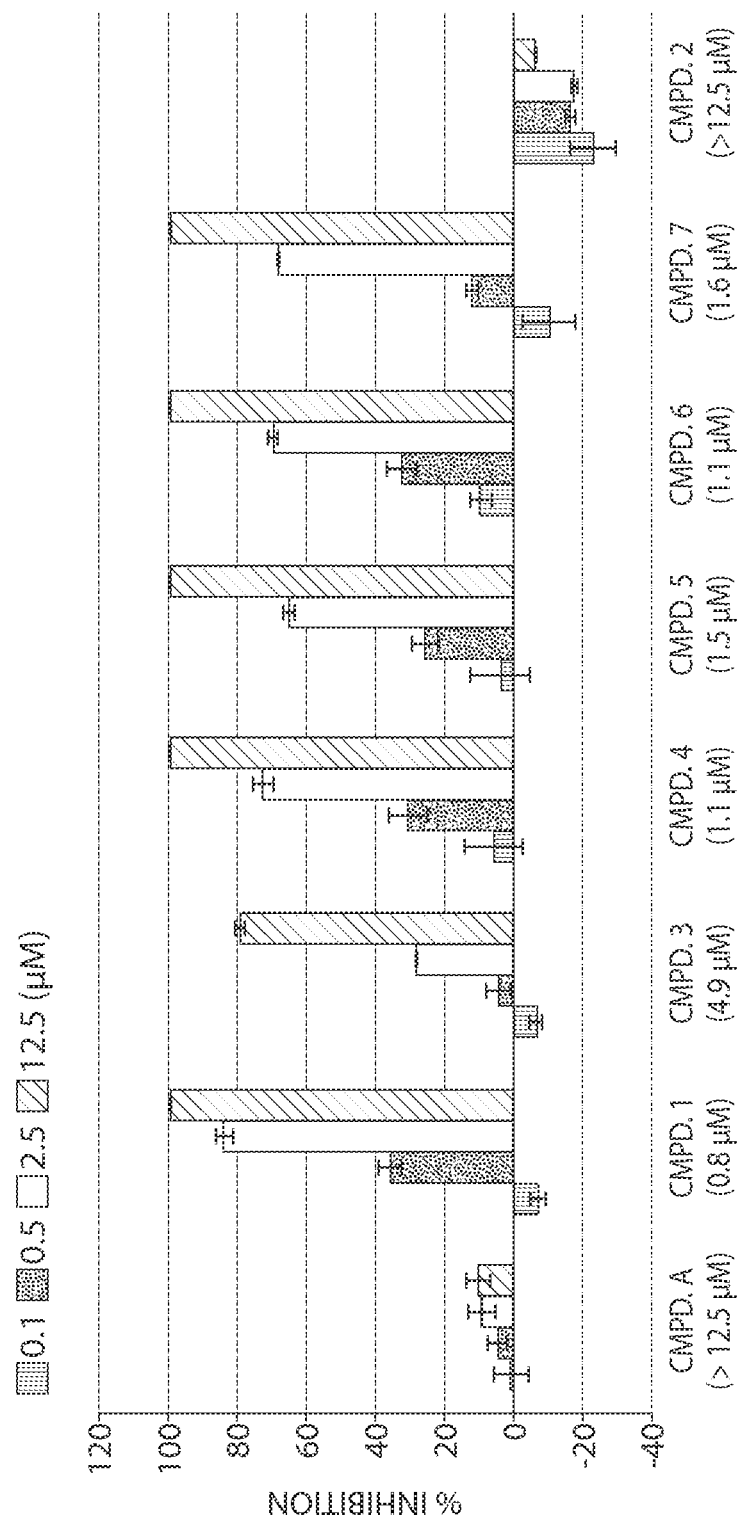
FIG. 1 shows the cytotoxicity of compounds 1 and 2 in confluent M14 cells.
Figure 2:
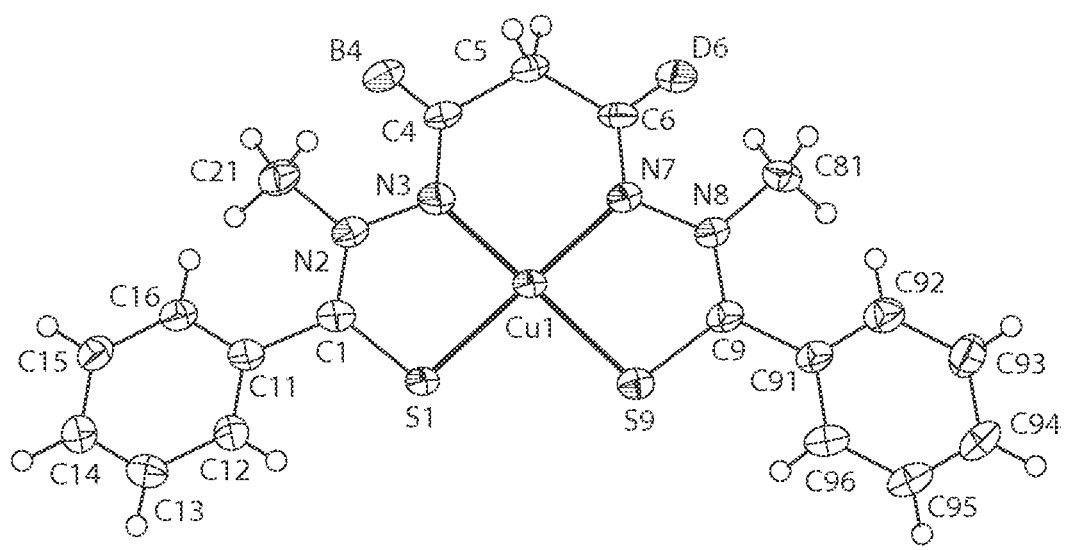
FIG. 2 is an ORTEP diagram of compound 1 showing 50% thermal ellipsoids.
Figure 3:
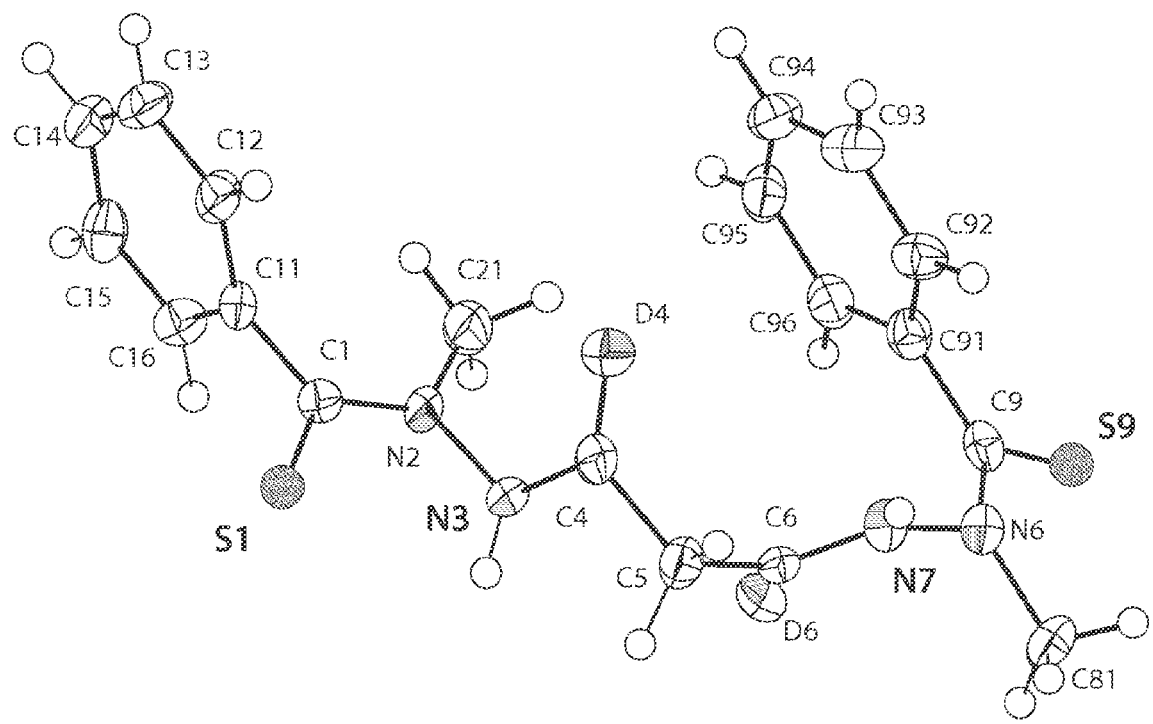
FIG. 3 is a structure showing nonplanar conformation of elesclomol predicted by energy-minimization.

The level of baseline lactate dehydrogenase (LDH) in the plasma is routinely measured in treatment of a variety of diseases, including melanoma; and in clinical trials of experimental cancer drugs. Elevated LDH levels, e.g., in plasma, are frequently indicative of disease severity or progression. Determining whether LDH levels are elevated (or not) in a patient or patient population is a routine matter to those of ordinary skill in the art. In an embodiment of the invention, an effective amount of a bis[thiohydrazide amide] compound is administered to a patient that has been determined to have normal to low lactate dehydrogenase levels. Such determination may be made on plasma levels of LDH from the patient, or a diagnosis that the patient is at risk of having cancer cells with elevated lactate dehydrogenase levels.

As set forth in further detail in Example 3, bis[thiohydrazide amide] compounds such as described herein are surprisingly found to be more effective in so-called "low-LDH" or "normal-LDH" patients than in so-called "high-LDH" patients. Without wishing to be bound to a particular theory or interpretation, it is believed that cancer cells undergoing high amount of glycolytic activity, i.e., high LDH conditions, are more resistant to bis[thiohydrazide amide] compounds than those same cells having lower levels of glycolytic activity.

In another embodiment of the invention, patients determined to have elevated lactate dehydrogenase levels may be treated with bis[thiohydrazide amide] compounds described herein in combination or co-treatment with an effective amount of an LDH inhibitor. LDH inhibitors, such as oxamate, gossypol, 3-hydroxyisoxazole-4-carboxylic acid (HICA), 4-hydroxy-1,2,5-thiadiazole-3-carboxylic acid (HTCA), derivatives of 8-deoxyhemigossylic (2,3-dihydroxynaphtalen-1-carboxylic) acid, such as FX11, and certain N-hydroxyindole-based inhibitors set forth in Granchi et al., J. Med. Chem. 2011, 54, 1599-1612 have been found (as in the example of oxamate set forth in further detail in Example 3) to attenuate, eliminate or reverse the deleterious effect on the activity and effect of high LDH levels on the bis[thiohydrazide amide] compounds.

"Baseline" refers to the level of LDH upon patient entrance into a study and is used to distinguish from levels of LDH the patient might have during or after treatment.

"Elevated" or "lower" refers to a patient's value relative to the upper limit of normal ("ULN") or the lower limit of normal ("LLN") which are based on historical normal control samples. As the level of LDH present in the subject will be a result of the disease, and not a result of treatment, typically not a control, a sample obtained from the patient prior to onset of the disease will not likely be available. Because different labs may have different absolute results, LDH values are presented relative to that lab's upper limit of normal value (ULN). LDH can be expressed in IU/ml (International Units per milliliter). An accepted ULN for LDH is 234 IU/ml, however, this value is not universally accepted or applicable to all methods of detection of LDH in all samples.

The specific value for ULN and LLN will also depend, for example, on the type of assay (e.g., ELISA, immunohistochemistry, imaging), the sample to be tested (e.g., serum, tumor tissue, urine), and other considerations known to those of skill in the art. The ULN or LLN can be used to define cut-offs between normal and abnormal. For example, a low level of LDH can be defined as a marker level less than or equal to the ULN for LDH, with a high level being all values greater than the ULN. Cut-offs can also be defined as fractional amounts of the ULN. For example, a low level of a marker can be understood to be a level of about 0.5 ULN or less, 0.6 ULN or less, 0.7 ULN or less, 0.8 ULN or less, 0.9 ULN or less, 1.0 ULN or less, 1.1 ULN or less, 1.2 ULN or less, 1.3 ULN or less, 1.4 ULN or less, 1.5 ULN or less, 1.6 ULN or less, 1.7 ULN or less, 1.8 ULN or less, 1.9 ULN or less, 2.0 ULN or less, 2.5 ULN or less, 3.0 ULN or less, or 4.0 ULN or less, with the corresponding high level of LDH being a value greater than the low level. In certain embodiments, the presence of a low level of LDH in a subject sample as defined above can be indicative that a subject will or will not respond to a particular therapeutic intervention. In certain embodiments, the presence of a high level of LDH in a subject sample as defined above can be indicative that a subject will or will not respond to a particular therapeutic intervention.

LDH levels can also be further stratified, for example, into low, intermediate, and high, based on the ULN value. For example, the presence of a low level of LDH in a subject sample as defined above can be indicative that a subject will or will not respond to a particular therapeutic intervention. An intermediate level of LDH, e.g., a range bracketed by any range within the values of 0.5 ULN, 0.6 ULN, 0.7 ULN, 0.8 ULN, 0.9 ULN, 1.0 ULN, 1.1 ULN, 1.2 ULN, 1.3 ULN, 1.4 ULN, 1.5 ULN, 1.6 ULN, 1.7 ULN, 1.8 ULN, 1.9 ULN, and 2.0 ULN, can be considered an intermediate range wherein the level of the marker may be indeterminate that a subject will or will not respond to a particular therapeutic intervention. A high level, greater than the intermediate level, would be indicative that a subject will or will not respond to a particular therapeutic intervention.

Similarly, cut-offs of ratios of LDH subunits or isoforms comparing the ULN, the LLN, or the median values to differentiate between high and low levels of hypoxia can be defined as any value or range bracketed by the values 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, or higher.

In certain embodiments, a "high" level of LDH is at least about 0.8 ULN or 1.0 ULN. In certain embodiments, a "low" level of LDH is less than about 0.8 ULN or 1.0 ULN. In certain embodiments, a high level of LDH is a normalized ratio of at least one, and a low level of LDH is a level of one or less.

The methods described herein include the use of transition metal complexes (coordinates or chelates) of a bis[thiohydrazide amide] compound. As used herein, "complexed" means that the bis[thiohydrazide amide] or a prodrug, isomer, ester, salt, hydrate, solvate, polymorph or deprotonated form thereof attaches to the transition metal ion through one or more coordinate covalent bonds or coordination bonds.

As used herein, "chelated" means that the bis[thiohydrazide amide] or a prodrug, isomer, ester, salt, hydrate, solvate, polymorph or deprotonated form thereof binds to the transition metal ion at two or more attachment points through coordinate covalent bonds or coordination bonds.

As used herein, "coordinate", "coordinated", "coordinate covalent bond" and "coordination bond" have the meanings that are commonly known to one of ordinary skill in the art.

As used herein, a "deprotonated form" of bis[thiohydrazide amide] refers to a molecule wherein one or more protons from the bis[thiohydrazide amide] or a prodrug, isomer, ester, salt, hydrate, solvate or polymorph thereof were removed. For example, a deprotonated form of the bis[thiohydrazide amide] of Structural Formula (I) is represented by the following structural formula:

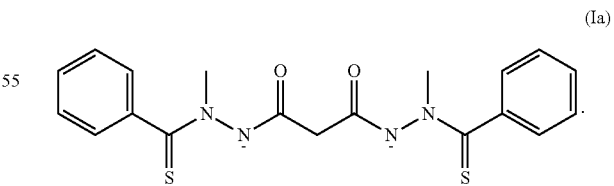

(Ia)

A "transition metal cation" refers to a positively charged ion of a metal in Groups 3-12 of the Periodic Table. Examples include $Ni^{2+}$, $Cu^+$, $Cu^{2+}$, $Co^{2+}$, $Co^{3+}$, $Fe^{2+}$, $Fe^{3+}$, $Zn^{2+}$, $Pt^{2+}$, $Pd^{2+}$, $V^{4+}$, $V^{5+}$, $Cr^{2+}$, $Cr^{3+}$, $Cr^{4+}$, $Mn^{2+}$, $Mn^{3+}$, $Mn^{4+}$ and $Mn^{5+}$. In a specific embodiment, the transition metal cations have a +2 charge. Examples include $Ni^{2+}$, $Cu^{2+}$, $Co^{2+}$, $Fe^{2+}$, $Zn^{2+}$, $Pt^{2+}$ and $Pd^{2+}$. In a specific embodiment, the transition metal cation is $Cu^+$, $Cu^{2+}$ or $Ni^{2+}$. In a more specific embodiment, the transition metal cation is $Cu^{2+}$. The molar ratio of bis[thiohydrazide amide] or a prodrug, isomer, ester, salt, hydrate, solvate, polymorph or a deprotonated form thereof to transition metal cation recited in this paragraph is, for example, equal to or greater than 0.5 and equal to or less than 2.0 (i.e., 0.5≤ratio≤2.0) or 1:1.

Exemplary compounds include Compound 1 and Compound 2:

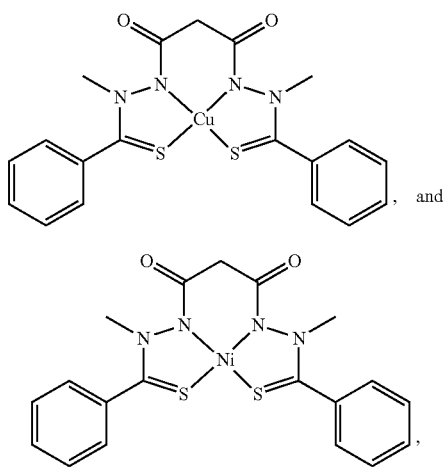

or a prodrug, isomer, ester, salt, hydrate, solvate or polymorph thereof.

Compounds used herein are advantageously in substantially pure form, e.g., greater than 50%, 60%, 70%, 80%, 90%, 95%, 97%, 99%, 99.5% or 99.9% pure by weight. "Percent purity by weight" means the weight of the compound divided by the weight of the compound plus impurities times 100%.

The compounds described herein may be prepared by reacting the bis[thiohydrazide amide] represented by Structural Formula (I) or a prodrug, isomer, ester, salt, hydrate, solvate, polymorph or a deprotonated form thereof with a transition metal salt. The transition metal salt can be any inorganic or organic salt of the transition metal cation. For example, chloride salt, nitrate salt, sulfate salt, acetate salt and the like can be reacted with a bis[thiohydrazide amide] or a prodrug, isomer, ester, salt, hydrate, solvate, polymorph or a deprotonated form thereof described herein to afford the compounds of the present invention. In one embodiment, the transition metal salt is a copper(II) salt, such as $CuCl_2$. In another embodiment, the transition metal salt is a nickel(II) salt, such as $NiCl_2.6H_2O$.

The ratio of the bis[thiohydrazide amide] and the transition metal cation source used is typically in the range of 0.5 to 2.0 or 0.8 to 1.2. In one embodiment, the ratio is about 1.

Solvents, such as methylene chloride, acetonitrile, acetone, alcohols (such as methanol, ethanol) tetrahydrofuran and water can be used in the reaction of the bis[thiohydrazide amide] derivative with the transition metal salts. In one embodiment, the solvent is ethanol.

The bis[thiohydrazide amides] used to prepare compounds described herein can be prepared according to methods described in U.S. Pat. Nos. 6,800,660, 6,762,204, and 6,825,235, and U.S. Publication No. 2008/0146842. The entire teachings of these patents and publications are incorporated herein by reference.

The compounds described herein may be obtained as different isomers (e.g., stereoisomers, coordination isomers, linkage isomers, hydrate isomers, and the like). Isomeric forms of the disclosed compounds and both pure isomers and mixtures thereof, including racemic mixtures may be used. Isomers can be separated and isolated using any suitable method, such as chromatography.

The compounds described herein may contain one or more chiral centers and/or double bonds and, therefore, exist as stereoisomers, such as double-bond isomers (i.e., geometric isomers), enantiomers, or diastereomers. The chemical structures depicted herein encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, "bis[thiohydrazide amide] compound" refers to compounds bis[thiohydrazide amide] compounds disclosed in U.S. Pat. Nos. 6,800,660; 6,762,204; 7,037,940; 7,001,923; and 6,924,312; International Patent Application No. PCT/US2009/066211, and U.S. application Ser. Nos. 12/310,304, 12/310,299, 12/310,303; the entire teachings of which are incorporated herein by reference.

As used herein, the term "polymorph" means solid crystalline forms of a compound described herein. Different polymorphs of the same compound can exhibit different physical, chemical and/or spectroscopic properties. Different physical properties include stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound that further includes a stoichiometric or non-stoichiometric amount of solvent bound by non-covalent intermolecular forces.

As used herein, the term "hydrate" means a compound that further includes a stoichiometric or non-stoichiometric amount of water bound by non-covalent intermolecular forces.

As used herein, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms.

The compounds described herein may be present in the form of salts. In one embodiment, the salts of the compounds of the invention refer to non-toxic "pharmaceutically acceptable salts." In another embodiment, the salts also include non-pharmaceutically acceptable salts, such as trifluoroacetate. Pharmaceutically acceptable salt forms include pharmaceutically acceptable acidic/anionic or basic/cationic salts.

Pharmaceutically acceptable acidic/anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

Compounds described herein may include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

"Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, ameliorating or improving a clinical symptom or indicator associated with a cancer (such as tissue or serum components) and/or reducing the likelihood of the cancer recurring once it has been removed or gone into remission.

The compounds disclosed herein surprisingly show sufficient anti-cancer activity to make them suitable for monotherapies, as well as in combination or in co-therapies with other anti-proliferative or anticancer therapies. In particular, it has been found that transition metal chelates, coordinates or complexes of N-malonyl-bis(N'-methyl-N'-thiobenzoylhydrazide) or a prodrug, isomer, ester, salt, hydrate, solvate, polymorph or deprotonated form thereof, can have sufficient anti-cancer activity to make them suitable for monotherapies, as well as in combination or in co-therapies with other anti-proliferative or anticancer therapies such as paclitaxel.

Other anti-proliferative or anticancer therapies may be combined with the methods disclosed herein. Examples include combination therapy with other anti-cancer drugs, surgery, radiotherapy (including gamma-radiation, neutron beam radiotherapy, electron beam radiotherapy, proton therapy, brachytherapy, and systemic radioactive isotopes), thermal therapy (see, for example, U.S. Publication No. 2008/0119440, the entire teachings of which are incorporated herein by reference) and endocrine therapy. Other anticancer agents that may be used include biologic response modifiers (including interferons, interleukins, and tumor necrosis factor (TNF)), hyperthermia and cryotherapy, agents to attenuate any adverse effects (e.g., antiemetics), and other approved chemotherapeutic drugs. Specific examples of anticancer agents are described in detail below. One co-administered anti-cancer drug may be an agent that stabilizes microtubules, such as paclitaxel or an analog of paclitaxel.

In one embodiment, the disclosed methods may be used to treat subjects with cancer, e.g., renal cancer, skin cancer, bone marrow cancer, blood cell cancer, prostate cancer, ovarian cancer, and breast cancer. Blood cell cancers include leukemia, lymphoma or myeloma. Leukemias include acute lymphocytic leukemia, acute myelocytic leukemia, chronic leukemia, polycythemia vera, lymphocytic leukemia, large granular lymphocytic leukemia, lymphoblastic leukemia, T-cell leukemia, T-lymphocytic leukemia, T-lymphoblastic leukemia, B cell leukemia, B-lymphocytic leukemia, B and T cell leukemia, B and T lymphocytic leukemia, myeloid leukemias, neutrophilic leukemia, eosinophilic leukemia, monocytic leukemia, myelomonocytic leukemia, Naegeli-type myeloid leukemia, and nonlymphocytic leukemia. Lymphomas include Hodgkin's and non-Hodgkin's disease, and Waldenström macroglobulinemia.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

As used herein, a "microtubulin stabilizer" means an anti-cancer agent which acts by arresting cells in the G2-M phases due to stabilization of microtubules. Microtubulin stabilizers can be used with the methods disclosed herein. Examples of microtubulin stabilizers include paclitaxel and paclitaxel analogs. Additional examples of microtubulin stabilizers include the following: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anti-cancer agent which acts by inhibiting tubulin polymerization or microtubule assembly. Microtubulin inhibitors can be used with the methods disclosed herein. Examples of microtubulin inhibitors include: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Therapeutic agents used in the methods disclosed herein may be administered simultaneously or separately. The exact details of the administration will depend on the pharmacokinetics of the two substances in the presence of each other, and can include administering two substances substantially at the same time, and one substance within a certain time period (e.g., within 24 hours) of administration of the other, if the pharmacokinetics are suitable. Designs of suitable dosing regimens are routine for one skilled in the art. In particular embodiments, two substances will be administered substantially simultaneously, i.e., within minutes of each other, or in a single composition that comprises both substances.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Suitable pharmaceutically acceptable carriers or diluents may contain inert ingredients which do not inhibit biological activity. The pharmaceutically acceptable carriers or diluents should be biocompatible, i.e., non-toxic, non-inflammatory, non-immunogenic and devoid of other undesired reactions upon the administration to a subject. Standard pharmaceutical formulation techniques can be employed, such as those described in *Remington's Pharmaceutical Sciences*, Mack Publishing Company, Easton, Pa. Formulation of the compound(s) to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art (Baker, et al., "Controlled Release of Biological Active Agents", John Wiley and Sons, 1986).

An "effective amount" is the quantity of compound in which a beneficial clinical outcome is achieved when the compound is administered to a subject. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the subject, such as general health, age, sex, body weight and tolerance to drugs. It may also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. In some embodiments, effective amounts of the disclosed compounds include microgram to milligram amounts of the compound per kilogram of subject or sample weight (e.g., about 1 µg/kg to about 500 mg/kg, about 500 µg/kg to about 250 mg/kg, about 1 mg/kg to about 100 mg/kg, about 10 mg/kg to about 50 mg/kg, and the like). When co-administered with another anti-cancer agent for the treatment of cancer, an "effective amount" of the second anti-cancer agent will depend on the type of drug used. Suitable dosages are known for approved anti-cancer agents and can be adjusted by the skilled artisan according to the condition of the subject, the type of cancer being treated and the compound being used.

The compounds and pharmaceutical compositions disclosed herein are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound and pharmaceutical composition disclosed herein can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

The present invention is illustrated by the following examples, which are not intended to be limiting in any way.

EXEMPLIFICATION

Example 1

Synthesis of the Compounds

Synthesis of Compound 1

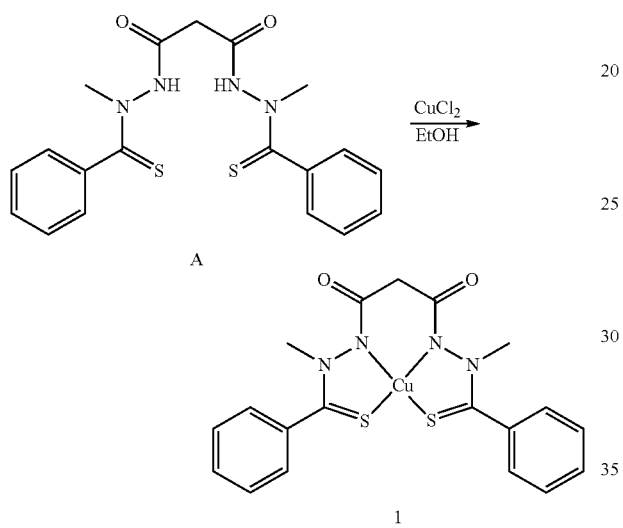

Copper(II) chloride (277 mg, 2.0 mmol) was added to a solution of bis[thiohydrazide amide] A (800 mg, 2.0 mmol) in EtOH (10.0 mL). The mixture was stirred at room temperature for 20 minutes. Water was then added. The solid was collected by filtration. The solid was taken up in methylene chloride. The resulting solution was washed with water (2×), dried ($Na_2SO_4$), filtered and concentrated to give crude solid. The solid was washed with acetone to give the pure compound 1 (600 mg). Single crystal solid were obtained by recrystallization from acetonitrile. MS (ESI) [M+H$^+$]: 462. MP: 198-202° C. (decomposed). Anal. calc. For $C_{19}H_{18}CuN_4O_2S_2$: C, 49.39; H, 3.93; N, 12.13. Found: C, 49.36; H, 3.68; N, 11.92.

| Table of Bond Distances in Armstrongs for Compound 1 | | |
|---|---|---|
| Atom 1 | Atom 2 | Distance |
| Cu1 | N7 | 1.944(2) |
| Cu1 | N3 | 1.948(2) |
| Cu1 | S1 | 2.2346(7) |
| Cu1 | S9 | 2.2375(7) |
| S1 | C1 | 1.694(3) |
| S9 | C9 | 1.707(3) |
| O4 | C4 | 1.231(3) |
| O6 | C6 | 1.227(3) |
| N2 | C1 | 1.321(3) |
| N2 | N3 | 1.405(3) |
| N2 | C21 | 1.482(3) |
| N3 | C4 | 1.370(3) |
| N7 | C6 | 1.363(3) |
| N7 | N8 | 1.414(3) |
| N8 | C9 | 1.316(3) |
| N8 | C81 | 1.481(3) |
| C1 | C11 | 1.479(4) |
| C4 | C5 | 1.510(4) |
| C5 | C6 | 1.519(4) |
| C5 | H51 | 0.94(4) |
| C5 | H52 | 1.01(3) |
| C9 | C91 | 1.481(4) |
| C11 | C12 | 1.392(3) |
| C11 | C16 | 1.394(3) |
| C12 | C13 | 1.383(4) |
| C12 | H12 | 0.950 |
| C13 | C14 | 1.389(4) |
| C13 | H13 | 0.950 |
| C14 | C15 | 1.389(4) |
| C14 | H14 | 0.950 |
| C15 | C16 | 1.384(4) |
| C15 | H15 | 0.950 |
| C16 | H16 | 0.950 |
| C21 | H21A | 0.980 |
| C21 | H21B | 0.980 |
| C21 | H21C | 0.980 |
| C81 | H81A | 0.980 |
| C81 | H81B | 0.980 |
| C81 | H81C | 0.980 |
| C91 | C92 | 1.391(4) |
| C91 | C96 | 1.403(3) |
| C92 | C93 | 1.388(4) |
| C92 | H92 | 0.950 |
| C93 | C94 | 1.382(4) |
| C93 | H93 | 0.950 |
| C94 | C95 | 1.393(4) |
| C94 | H94 | 0.956 |
| C95 | C96 | 1.384(4) |
| C95 | H95 | 0.950 |
| C96 | H96 | 0.950 |

Numbers in parentheses are estimated standard deviations in the least significant digits.

| Table of Bond Angles in Degrees for Compound 1 | | | |
|---|---|---|---|
| Atom 1 | Atom 2 | Atom 3 | Angle |
| N7 | Cu1 | N3 | 96.27(8) |
| N7 | Cu1 | S1 | 161.69(6) |
| N3 | Cu1 | S1 | 86.92(6) |
| N7 | Cu1 | S9 | 86.58(6) |
| N3 | Cu1 | S9 | 158.38(6) |
| S1 | Cu1 | S9 | 97.10(3) |
| C1 | S1 | Cu1 | 96.53(9) |
| C9 | S9 | Cu1 | 96.97(9) |
| C1 | N2 | N3 | 118.7(2) |
| C1 | N2 | C21 | 122.7(2) |
| N3 | N2 | C21 | 116.67(19) |
| C4 | N3 | N2 | 112.6(2) |
| C4 | N3 | Cu1 | 118.96(18) |
| N2 | N3 | Cu1 | 115.96(14) |
| C6 | N7 | N8 | 113.3(2) |
| C6 | N7 | Cu1 | 120.48(17) |
| N8 | N7 | Cu1 | 116.52(14) |
| C9 | N8 | N7 | 118.6(2) |
| C9 | N8 | C81 | 123.2(2) |
| N7 | N8 | C81 | 115.93(19) |
| N2 | C1 | C11 | 120.7(2) |
| N2 | C1 | S1 | 121.3(2) |
| C11 | C1 | S1 | 118.07(17) |
| O4 | C4 | N3 | 125.2(2) |
| O4 | C4 | C5 | 119.7(2) |
| N3 | C4 | C5 | 114.9(2) |
| C4 | C5 | C6 | 124.5(2) |
| C4 | C5 | H51 | 111(2) |

Table of Bond Angles in Degrees for Compound 1

| Atom 1 | Atom 2 | Atom 3 | Angle |
|---|---|---|---|
| C6 | C5 | H51 | 106(2) |
| C4 | C5 | H52 | 101.6(19) |
| C6 | C5 | H52 | 111.1(19) |
| H51 | C5 | H52 | 99(3) |
| O6 | C6 | N7 | 125.4(2) |
| O6 | C6 | C5 | 118.8(2) |
| N7 | C6 | C5 | 115.6(2) |
| N8 | C9 | C91 | 121.6(2) |
| N8 | C9 | S9 | 120.7(2) |
| C91 | C9 | S9 | 117.68(18) |
| C12 | C11 | C16 | 119.6(2) |
| C12 | C11 | C1 | 119.8(2) |
| C16 | C11 | C1 | 120.5(2) |
| C13 | C12 | C11 | 119.7(2) |
| C13 | C12 | H12 | 120.20 |
| C11 | C12 | H12 | 120.20 |
| C12 | C13 | C14 | 120.7(3) |
| C12 | C13 | H13 | 119.60 |
| C14 | C13 | H13 | 119.60 |
| C13 | C14 | C15 | 119.6(3) |
| C13 | C14 | H14 | 120.20 |
| C15 | C14 | H14 | 120.20 |
| C16 | C15 | C14 | 119.9(2) |
| C16 | C15 | H15 | 120.00 |
| C14 | C15 | H15 | 120.00 |
| C15 | C16 | C11 | 120.4(2) |
| C15 | C16 | H16 | 119.80 |
| C11 | C16 | H16 | 119.80 |
| N2 | C21 | H21A | 109.50 |
| N2 | C21 | H21B | 109.50 |
| H21A | C21 | H21B | 109.50 |
| N2 | C21 | H21C | 109.50 |
| H21A | C21 | H21C | 109.50 |
| H21B | C21 | H21C | 109.50 |
| N8 | C81 | H81A | 109.50 |
| N8 | C81 | H81B | 109.50 |
| H81A | C81 | H81B | 109.50 |
| N8 | C81 | H81C | 109.50 |
| H81A | C81 | H81C | 109.50 |
| H81B | C81 | H81C | 109.50 |
| C92 | C91 | C96 | 119.1(2) |
| C92 | C91 | C9 | 121.6(2) |
| C96 | C91 | C9 | 119.1(2) |
| C93 | C92 | C91 | 120.6(2) |
| C93 | C92 | H92 | 119.70 |
| C91 | C92 | H92 | 119.70 |
| C94 | C93 | C92 | 120.1(3) |
| C94 | C93 | H93 | 119.90 |
| C92 | C93 | H93 | 119.90 |
| C93 | C94 | C95 | 119.8(3) |
| C93 | C94 | H94 | 120.10 |
| C95 | C94 | H94 | 120.10 |
| C96 | C95 | C94 | 120.5(2) |
| C96 | C95 | H95 | 119.80 |
| C94 | C95 | H95 | 119.80 |
| C95 | C96 | C91 | 119.9(3) |
| C95 | C96 | H96 | 120.00 |
| C91 | C96 | H96 | 120.00 |

Numbers in parentheses are estimated standard deviation in the least significant digits.

Synthesis of Compound 2

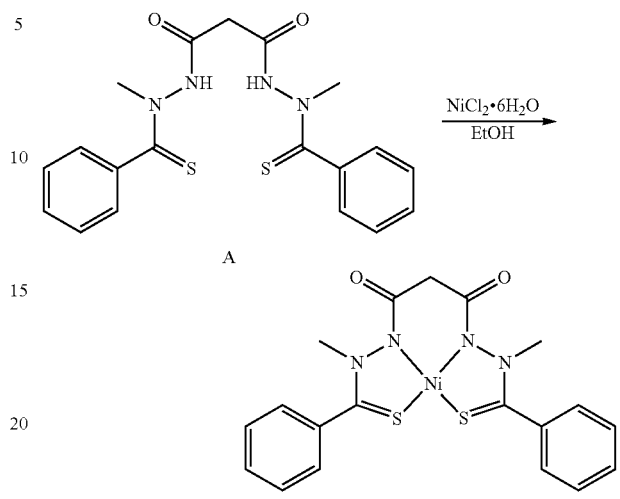

Compound 2 was prepared similarly as described for the preparation of compounds 1 using bis[thiohydrazide amide] A and nickel(II) chloride hexahydrate. MS (ESI) [M+H$^+$]: 457. $^1$H NMR (300 MHz, CDCl$_3$) δ 7.58-7.44 (m, 10H), 3.61 (s, 6H), 3.59 (s, 2H).

Example 2

Biological Activity of Compound 1

M14 melanoma cells were seeded at 50,000 cells per well of 96-well plate in 100 µl of Dulbecco's minimum essential medium (DMEM) supplemented with 10% fetal bovine serum. Cells were cultured at 37° C. under 5% CO2-95% air. After 16 hours of incubation, the test compound was added to the cell culture. The compound was first diluted in 100% dimethyl sulfoxide (DMSO) at 400-fold of the final concentrations actually used in the assay. The DMSO solution was next diluted 20 fold with the culture medium, and then finally added to the assay wells at another 20-fold dilution. Assay medium included the test compound with concentrations as indicated with 0.25% DMSO. Cell viability was measured with a CCK8 assay (as described in the Technical Manual for Cell Counting Kit-8, Product #CK04-11, CK04-13 and CK04-20, Dojindo Molecular Technologies, Inc. MD; Tantular, I. S. et al. Tropical Medicine and International Health, 8(6), 569-574, 2003) in the last 15 minutes after a 48 h incubation with the test compound. The data for compounds 1 and 2 are compared with that of compound A, shown in FIG. 1. Each bar of the figure expresses average percent inhibition against vehicle (0.25% DMSO) control (n=4). Error bars indicate standard deviation. The IC$_{50}$ values for compound A compound 2 are greater than 12.5 µM; while the IC$_{50}$ value for compound 1 is 0.8 µm.

Example 3

Bis[thiohydrazide amide] Compounds and Lactate Dehydrogenase Level

In a Phase 3 trial in metastatic melanoma, the level of baseline lactate dehydrogenase (LDH) in patients emerged as an important prognostic factor for treatment outcomes with elesclomol. A differential response to treatment with elesclomol was shown, based on the level of baseline LDH in the plasma, an established prognostic biomarker in melanoma and a pre-specified stratification variable in the trial. The primary endpoint of progression-free survival (PFS) was achieved in the normal LDH population, 68% of patients, with a significant improvement in median PFS (3.6 vs. 2.1 months, HR=0.76, p=0.027), an acceptable safety profile, and no impact on overall survival. In the elevated LDH population, 32% of patients, no difference was observed between the two arms of the trial for the primary endpoint (1.8 vs. 1.9 months, HR=1.10, p=0.549), and a negative impact was observed for the survival endpoint.

Elesclomol selectively chelates copper and generates ROS via reduction of Cu(II) to Cu(I). Because this copper redox reaction can be influenced by changes in cellular metabolic properties, the influence of the balance of mitochondrial respiration (normoxic conditions, normal LDH activity) and glycolysis (hypoxic conditions, high LDH activity) on elesclomol activity in the cancer cell was investigated. In this example, elesclomol activity was evaluated under several situations in which cells express high levels of LDH and mitochondrial respiration is reduced.

Figure 4:
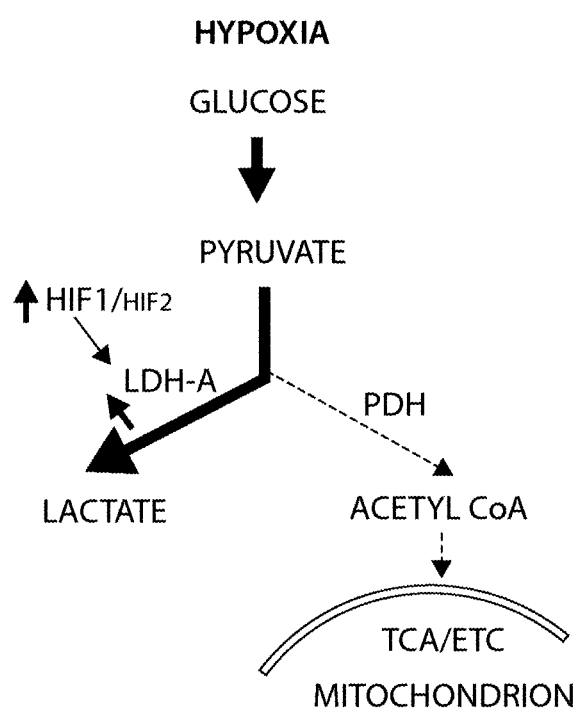
FIG. 4 is a graphical representation of how stabilized HIF-1α shunts away energy carbon flow from mitochondria under hypoxic conditions.
Figure 5A:
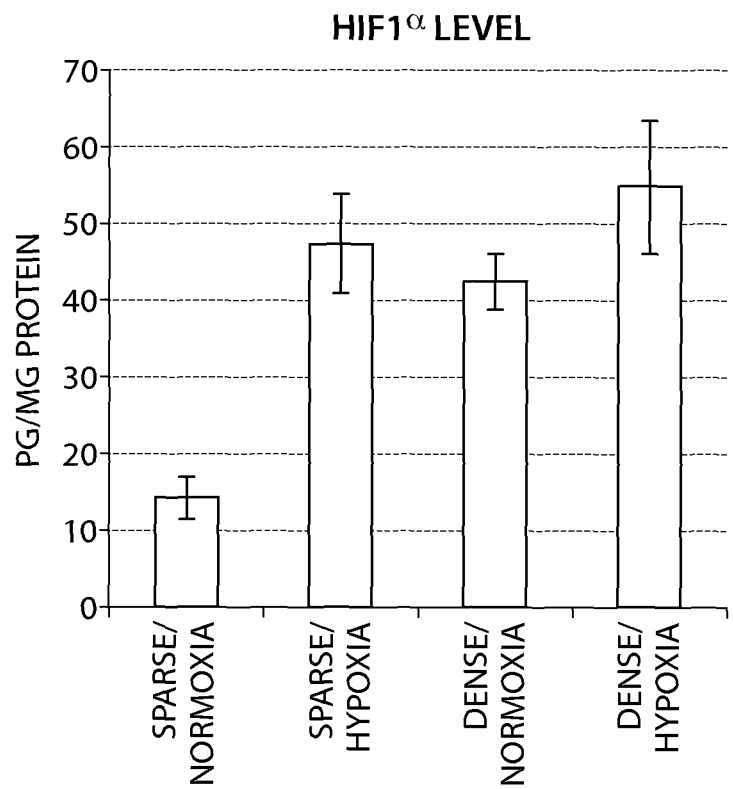
FIGS. 5a-5b illustrate the reduced potency of the bis[thiohydrazide amide] compound elesclomol in melanoma cells when HIF-1α is high, based on experiments detailed in Example 3.
Figure 5B:
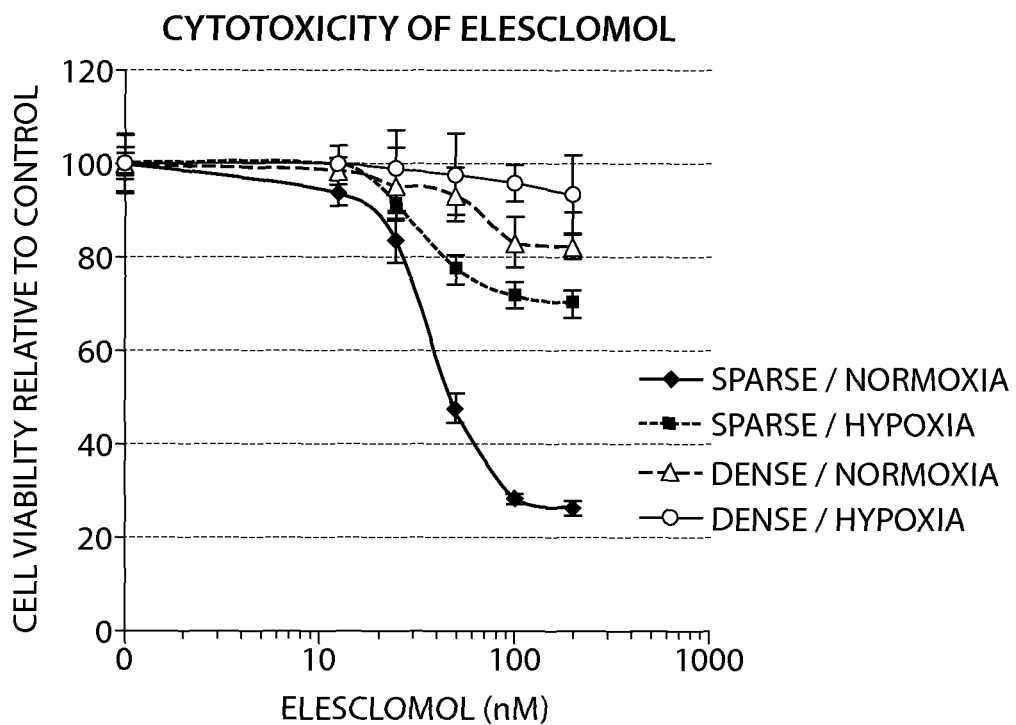

In hypoxic cells, stabilized HIF-1α shunts away energy carbon flow from mitochondria (illustrated graphically in FIG. 4.). The regulatory subunit of HIF-1α is stabilized under hypoxic conditions, and thus-stabilized HIF-1α forms active HIF-1 (HIF-1α/1b heterodimer), whereupon HIF-1 induces LDH-A to convert pyruvate to lactate. The potency of the bis[thiohydrazide amide] compound elesclomol on sparse and dense melanoma cells was assayed under hypoxic and normoxic conditions. Total HIF-1α (cytosolic+nuclear, FIG. 5a) and cell viability of M14 (MDA-MB-435) melanoma cells (FIG. 5b) was evaluated at 12 h and 48 h by ELISA (R&D systems) and cellular ATP levels (CellTiter Glo-Promega), respectively, under normoxia (20%) or hypoxia (0.1%) with sparse (2 k cells/well) or dense (20 k cells/well) in 96-well plates. The increased potency of elesclomol under normoxic conditions is best seen in FIG. 5b.

Figure 6A:
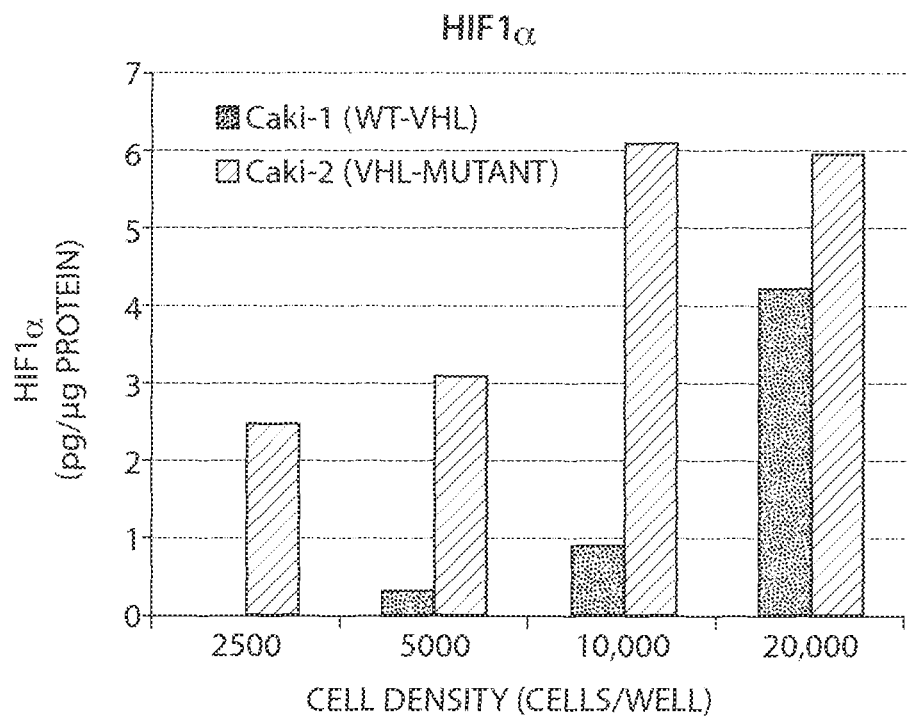
FIGS. 6a-6b illustrate HIF-1α-high Caki-2 cells' elesclomol resistance, HIF-1α-low Caki-1 cells' elesclomol sensitivity, based on experiments detailed in Example 3.
Figure 6B:
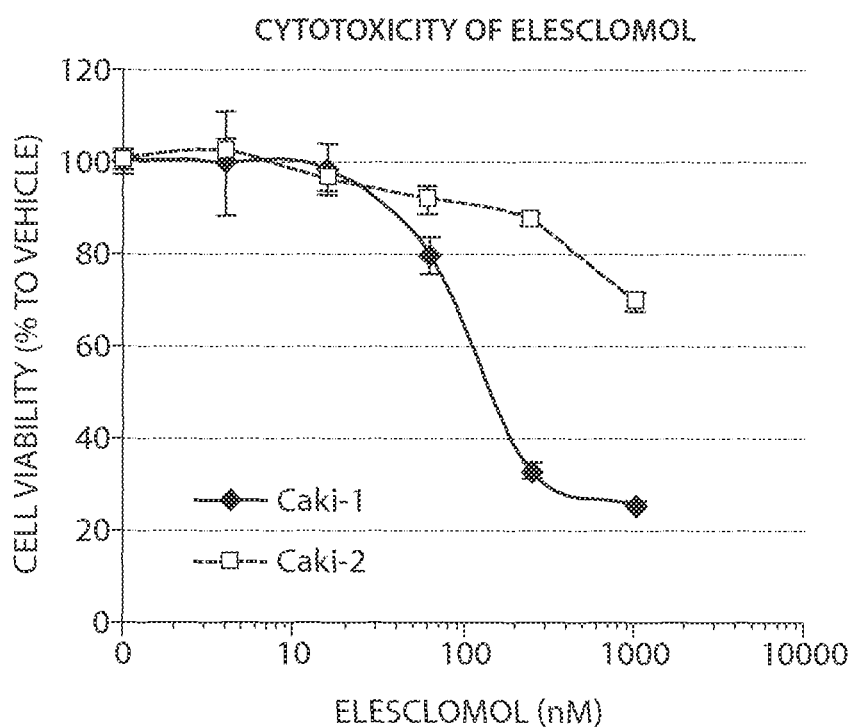
Figure 7A:
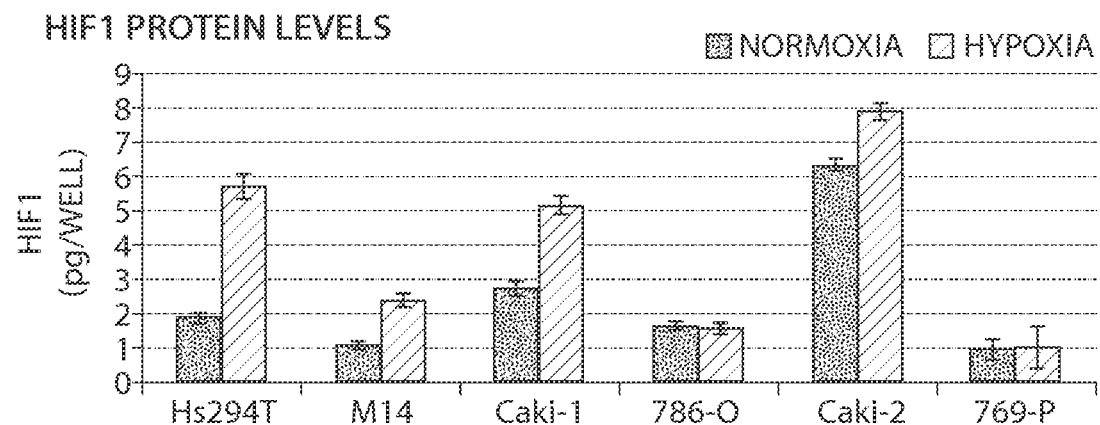
FIGS. 7a-7d illustrate how high HIF-1α protein and LDH-A activity levels correlate with the reduced sensitivity to elesclomol, based on experiments detailed in Example 3.
Figure 7B:
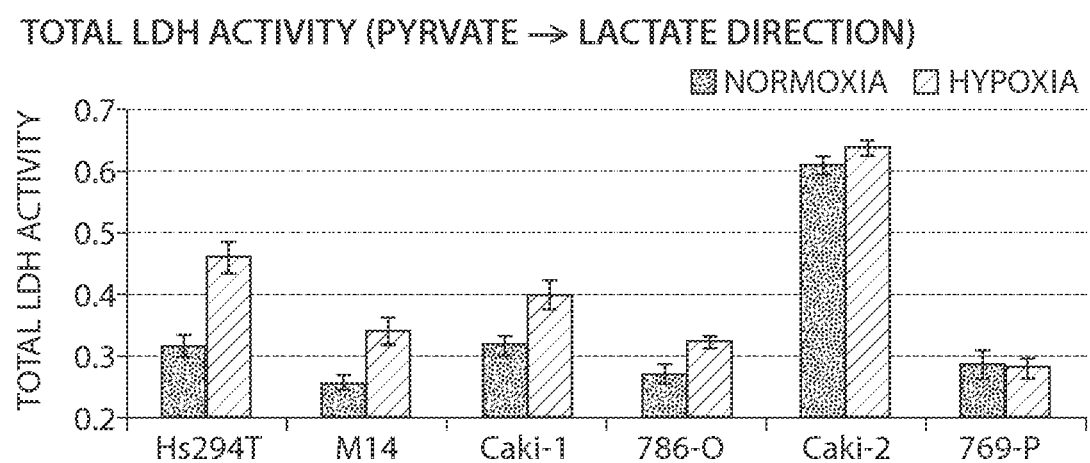
Figure 7C:
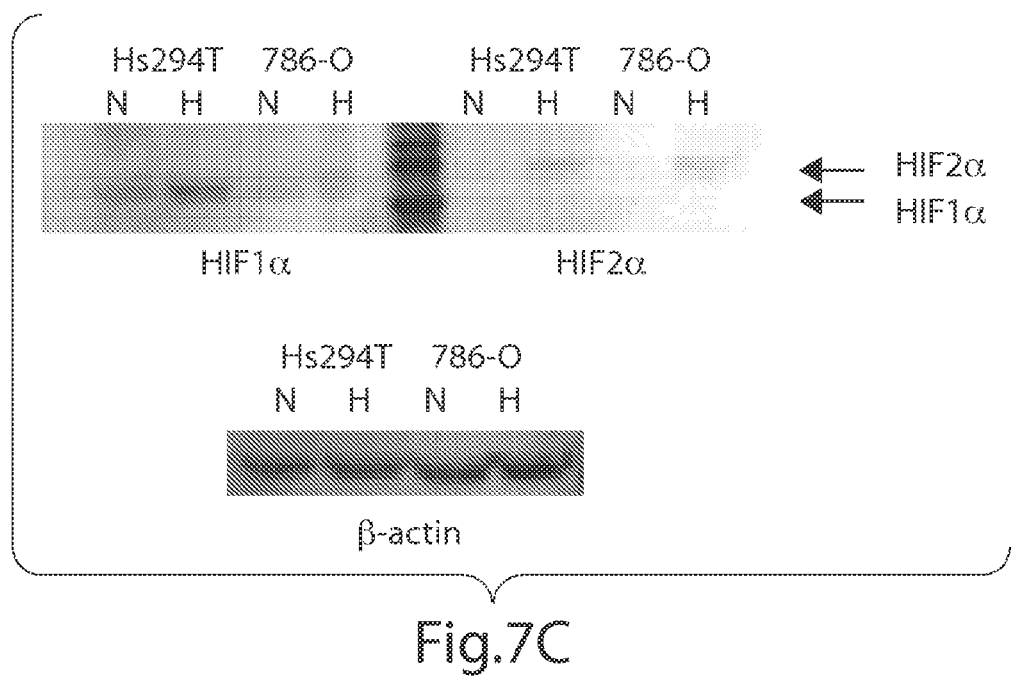
Figure 7D:
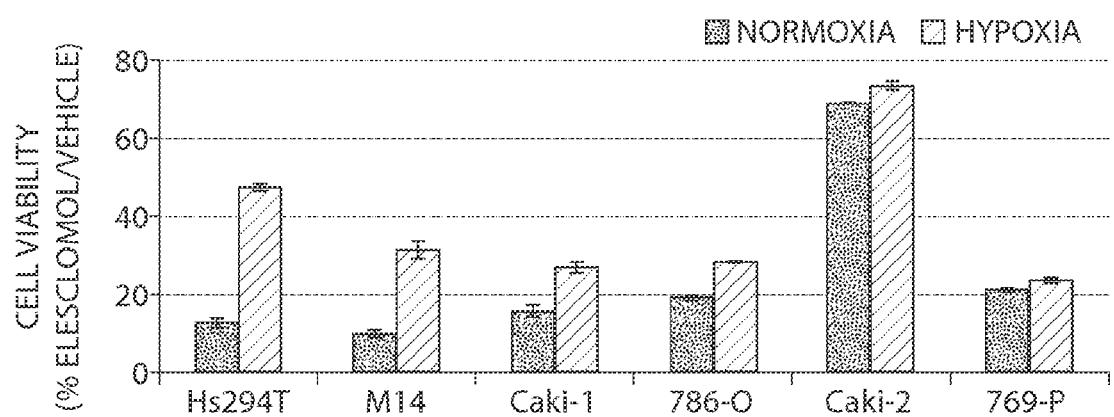

To further investigate a correlation between HIF-1α and elesclomol potency, lines within the same cancer phenotype but showing distinct levels of HIF1α were evaluated. Caki-1 and -2 are renal cancer cell lines established from the same patient; Caki-2 cells constitutively express HIF-1α while the expression in Caki-1 cells is conditional. VHL protein is a negative regulator of HIF-1α, and a VHL mutation accompanies constitutive HIF-1α expression. In FIG. 6a, cells were serially diluted to the densities indicated. Cell lysates were harvested for ELISA at 24 h after seeding. In FIG. 6b, cells were seeded at 2,500 cells/well-96 plate. Cell viability was evaluated by CellTiter Glo ATP assay at 24 h. As seen in FIG. 6b, the HIF-1α-high Caki-2 cells are resistant to elesclomol, while HIF-1α-low Caki-1 cells are sensitive to elesclomol.

FIG. 7 illustrates experimental work done with a variety of cells showing how high levels of HIF-1α and LDH-A activity correlate with the reduced sensitivity to elesclomol. FIGS. 7a and 7b show the reductive (i.e., pyruvate to lactate) LDH activity and HIF-1α level under normoxic and hypoxic conditions. The cells set forth in the Figures and in Table 1, below were seeded at 2 k cells/well in a 96-well plate and cultured under normoxic (20% $O_2$) and hypoxic (0.1% $O_2$) conditions to determine their LDH activity and HIF-1α level. LDH-A activity (measuring reduction of pyruvate to lactate by monitoring NADH at 340 nm) and HIF-1α were analyzed at 24 h. FIG. 7c shows HIF-1α and HIF-2α induced by hypoxia: immunoblots were carried out with mouse monoclonal anti-HIF-1α (R&D System) and rabbit anti-HIF-2α (Abcam) antibodies. An experiment was then run to treat these same cell lines with vehicle or 50 nM elesclomol under normoxic (20% $O_2$) and hypoxia (0.1% $O_2$) conditions for 36 h (FIG. 7d.) Cell viability was evaluated by cellular ATP (CellTiter Glo, Promega).

As seen in Table 1, LDH-A activity increased in most of the cell lines under hypoxic conditions (786-O cells increased LDH-A activity under hypoxic conditions with an increase in HIF-2α, another HIF that increases LDH-A). The 769-P cell line, which did not elevate LDH-A activity under hypoxic conditions, showed no change in its sensitivity to elesclomol.

TABLE 1

Summary of correlation of HIF-1α and LDH-A with activity of elesclomol

| Cell line | Tissue | VHL* | HIF-1α Normoxia | LDH-A Normoxia | Viability w/ elesclomol Normoxia | HIF-1α Hypoxia | LDH-A Hypoxia | Viability w/ elesclomol Hypoxia |
|---|---|---|---|---|---|---|---|---|
| Hs294T | melanoma | WT | − | − | − | + | + | + |
| M14 | melanoma | WT | − | − | − | + | + | + |
| Caki-1 | renal cancer | WT | − | − | − | + | + | + |
| 786-O | renal cancer | null | − | − | − | −(HIF-2α+) | + | + |
| Caki-2 | renal cancer | mutant | ++ | ++ | ++ | ++ | ++ | ++ |
| 769-P | renal cancer | WT | − | − | − | −(HIF-2α−) | − | − |

*negative regulator of HIF-1α

Figure 8:
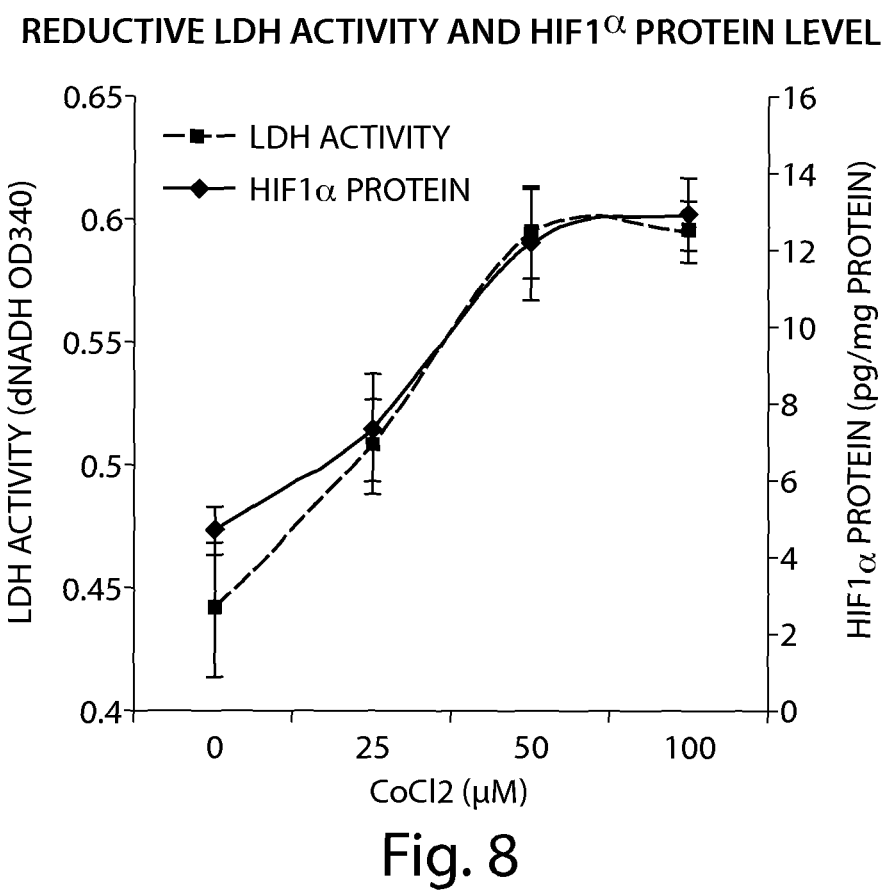
FIG. 8 shows how $CoCl_2$, a chemical mimetic of hypoxia, increased HIF-1α by stabilizing HIF-1α protein, resulting in increased reductive LDH activity, based on experiments detailed in Example 3.

The influence of hypoxia on HIF-1α levels can be illustrated through the use of $CoCl_2$, a chemical mimetic of hypoxia. As seen in FIG. 8, $CoCl_2$ increases HIF-1α by stabilizing HIF-1α protein resulting in increased reductive LDH activity. LDH-A activity (measuring reduction of pyruvate to lactate by monitoring NADH at 340 nm) and HIF-1α was analyzed after 24 h incubation of M14 melanoma cells with the indicated concentration of $CoCl_2$.

Figure 9A:
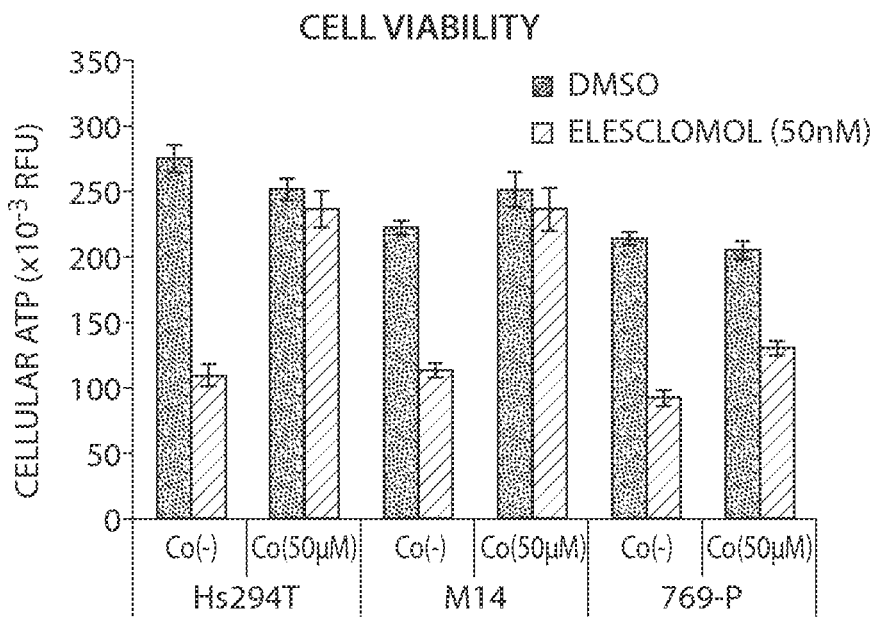
FIGS. 9a-9d illustrate how an increase in LDH-A activity results in a reduction in the sensitivity to elesclomol, based on experiments detailed in Example 3.
Figure 9B:
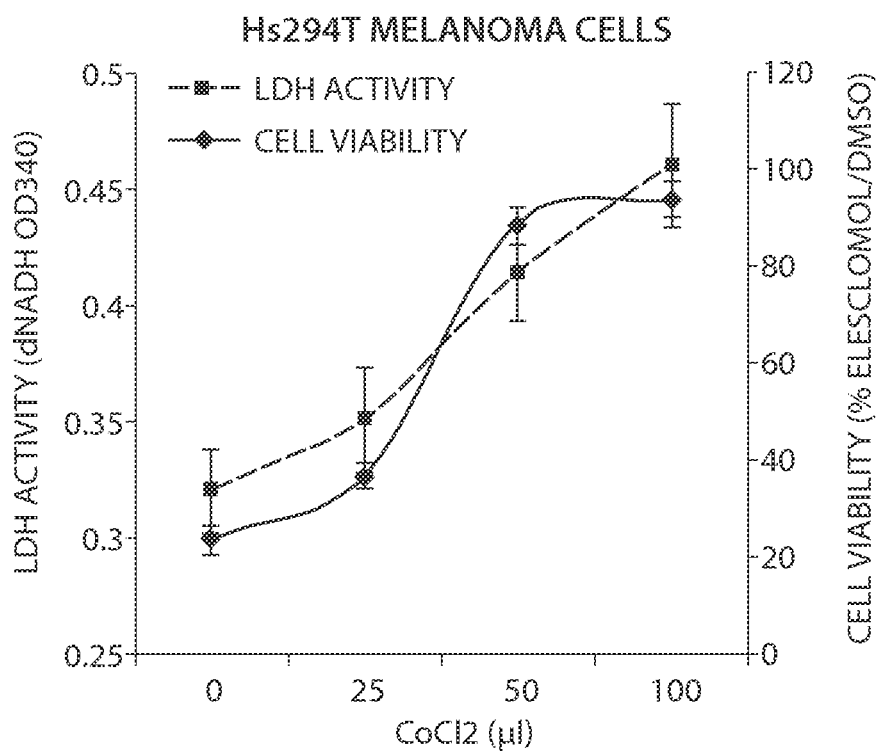
Figure 9C:
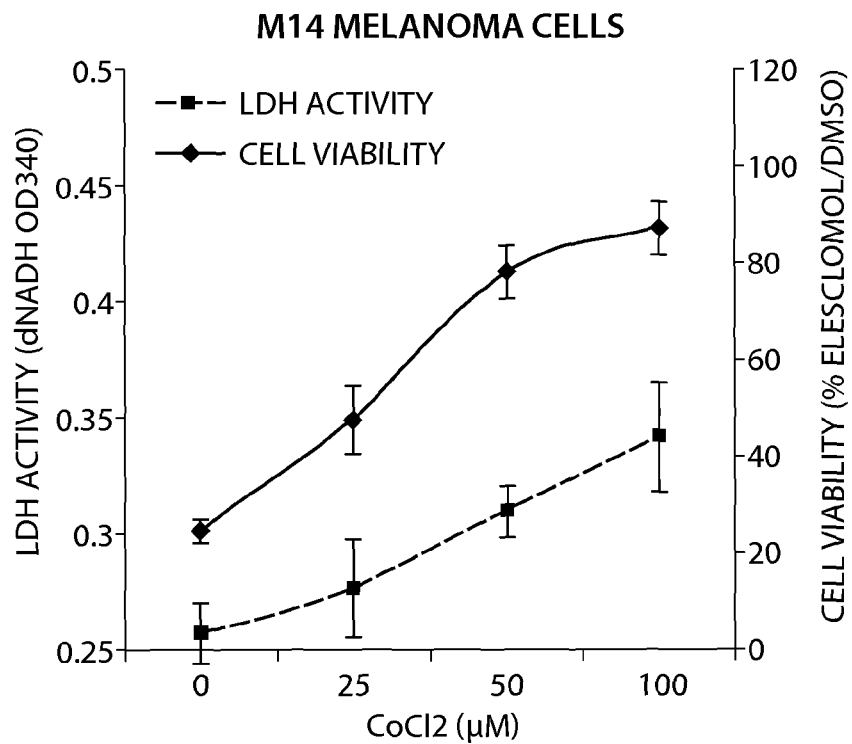
Figure 9D:
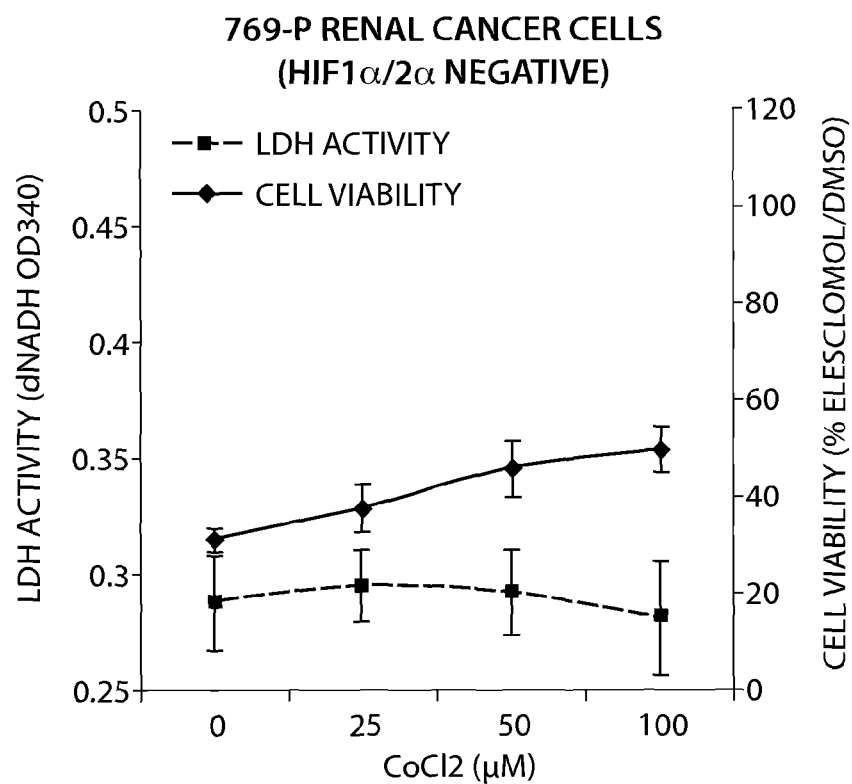

The effect of an increase in LDH-A activity on elesclomol potency was measured in a variety of cells. FIG. 9a illustrates the effect of hypoxic conditions on elesclomol potency in Hs294T, M4, and 769-P cells that have been treated with $CoCl_2$. In FIGS. 9b-9d, LDH-A activity and cell viability was assessed in Hs294T, M4, and 769-P, respectively. LDH-A activity was assessed after 24 h incubation with the indicated concentration of $CoCl_2$. Cell viability with or without 50 nM elesclomol in the presence of $CoCl_2$ was evaluated at 48 h.

Figure 10:
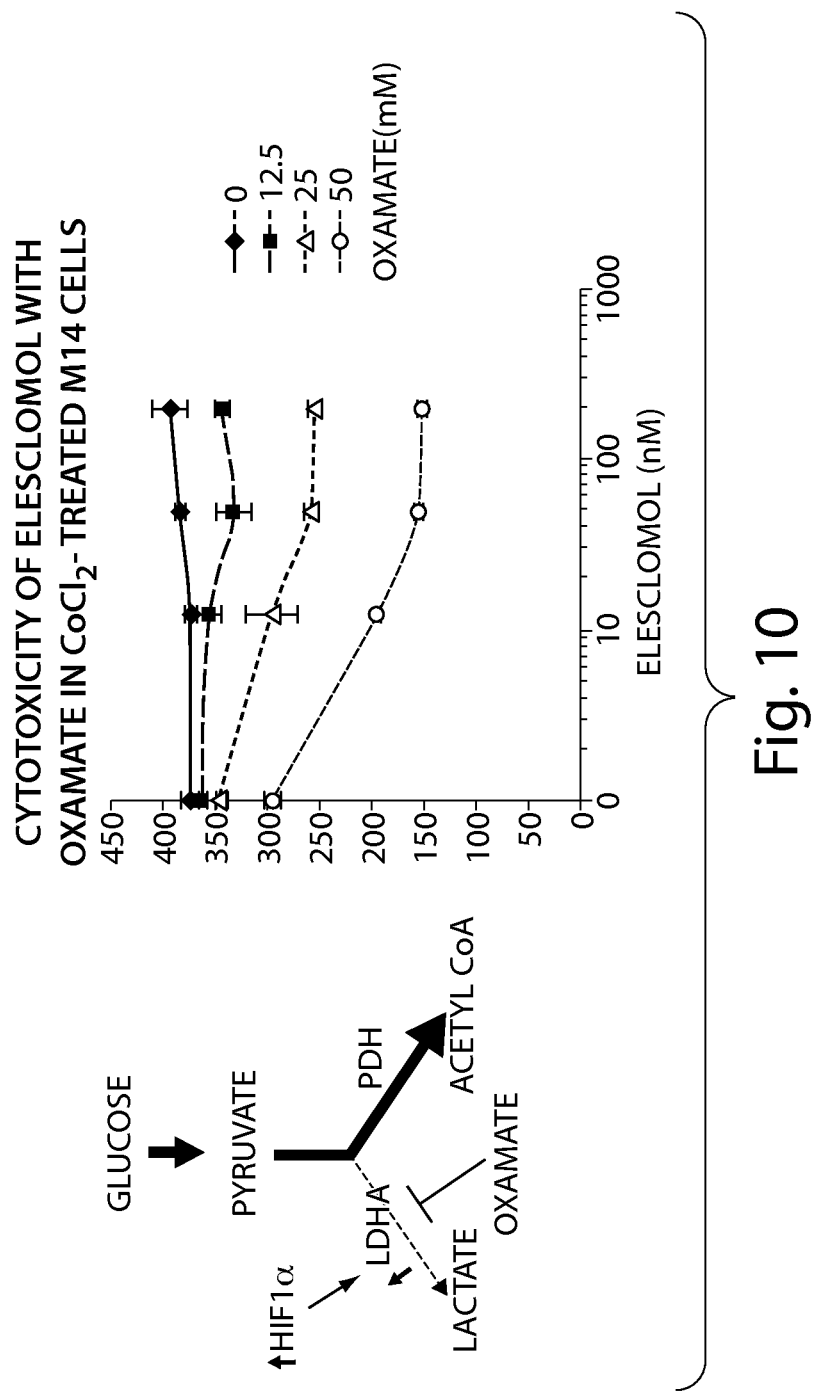
FIG. 10 shows how the LDH-A inhibitor oxamate, a pyruvate analog, restores the activity of elesclomol in $CoCl_2$-treated M14 cells, based on experiments detailed in Example 3.

To determine whether the deleterious effects of hypoxia on elesclomol activity was due to LDH being present in higher than normal amounts, experiments were conducted to see if an LDH inhibitor had an effect on elesclomol cytotoxicity. By inhibiting LDH, the conversion of pyruvate to lactate is shut down, as illustrated in the left panel of FIG. 10. Oxamate, a pyruvate analog and LDH-A inhibitor, was tested on $CoCl_2$- treated M14 cells as illustrated in the right panel of FIG. 10. Cell viability was assessed after 48 h incubation with or without elesclomol and oxamate. As seen in FIG. 10, addition or co-administration of an LDH inhibitor restores the activity of elesclomol in CoCl$_2$-treated M14 cells.

Figure 11:
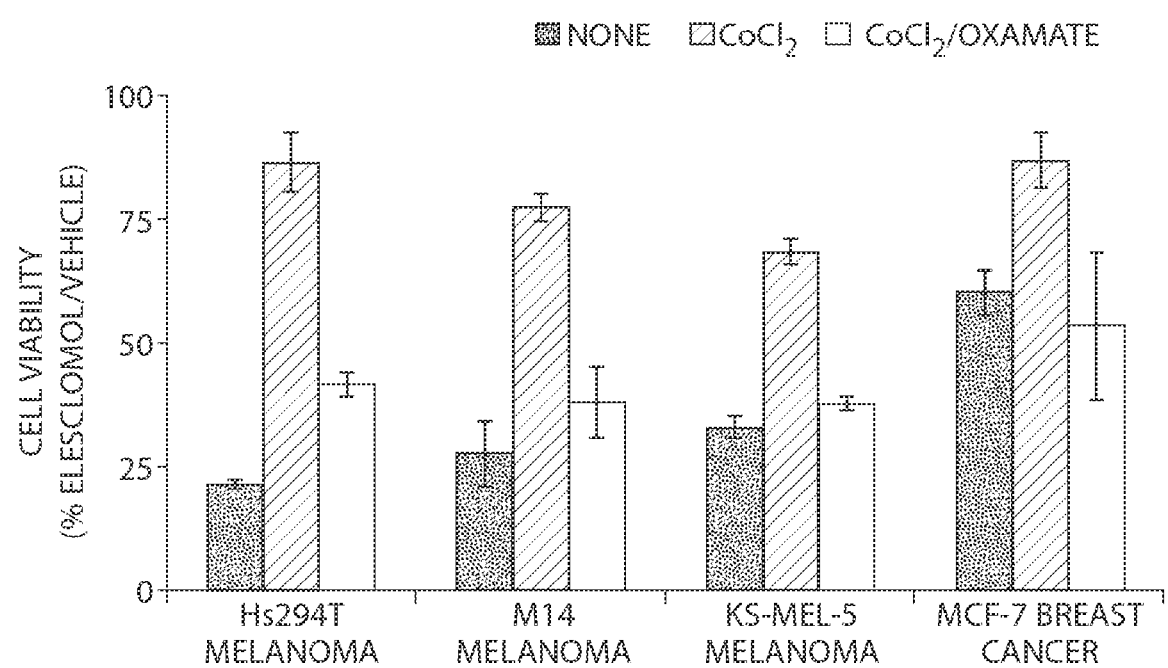
FIG. 11 shows how elesclomol remains active in $CoCl_2$-treated cells when co-treated with the LDH-A inhibitor oxamate, based on experiments detailed in Example 3.
Figure 12:
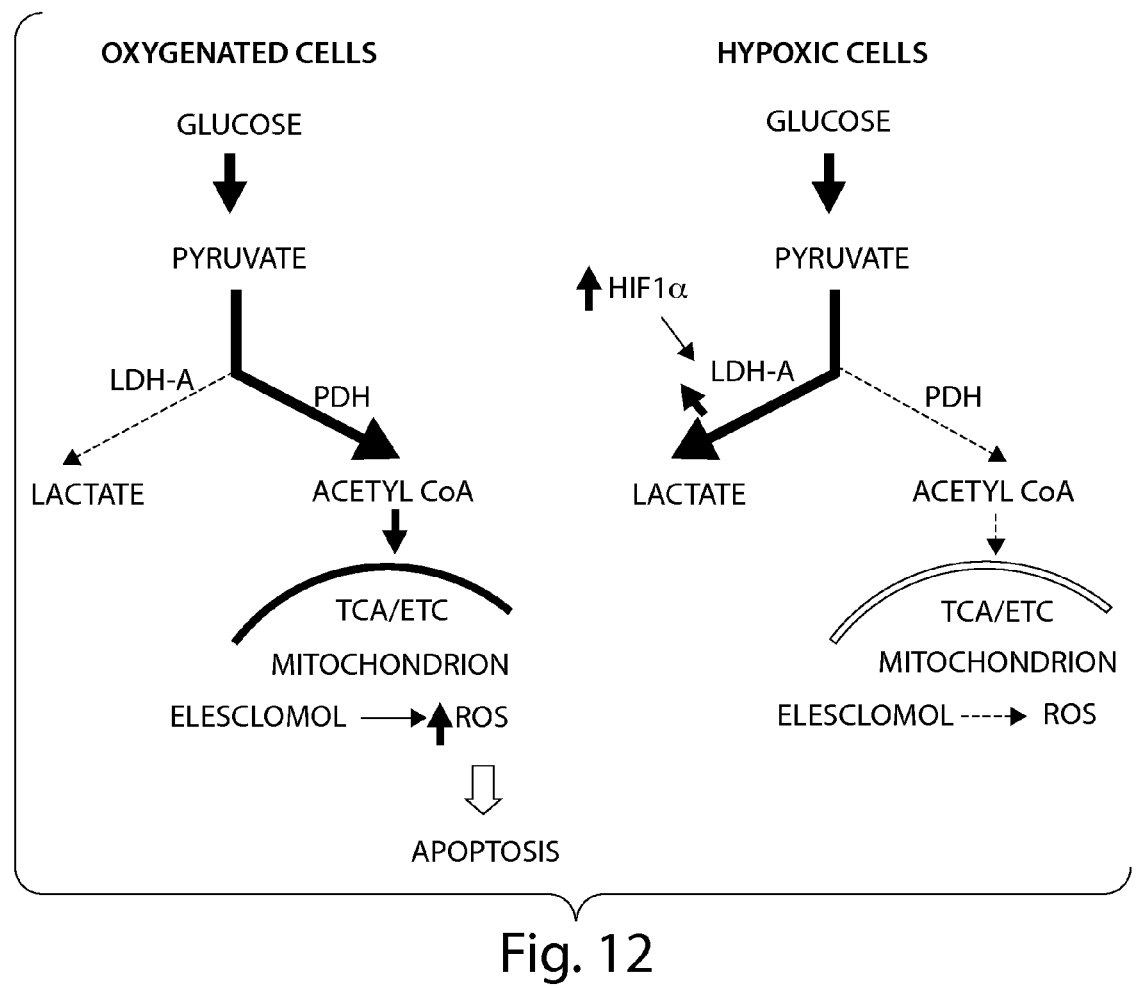
FIG. 12 is a graphical representation summarizing the mitochondrial activity-dependent toxicity of the bis[thiohydrazide amide] compound elesclomol.

Further proof of the beneficial effect of co-treatment of elesclomol and an LDH-A inhibitor (oxamate) is illustrated in FIG. 11, showing that elesclomol remains active in CoCl$_2$-treated cells upon co-treatment. Cell viability was assessed after 48 h incubation with or without 50 nM elesclomol in the presence or absence of 50 μM CoCl$_2$ and 25 mM oxamate.

Thus, a clear correlation was observed between the activity of elesclomol and LDH-A levels. Elesclomol activity is restored in LDH-A-high cancer cells by an LDH-A inhibitor, oxamate, suggesting that elesclomol is more active in cells where energy production is primarily through the mitochondrial respiration (normoxic conditions; normal LDH-A) and less active in cells where energy production occurs primarily through glycolysis (hypoxic conditions; high LDH-A.) These observations are consistent with results from the Phase 3 clinical trial noted above, in which elesclomol showed anticancer activity in the normal LDH patient population but not in the elevated LDH population.

REFERENCES

Berkenblit A, Eder J P, Jr., Ryan D P, Seiden M V, Tatsuta N, Sherman M L, Dahl T A, Dezube B J, Supko J G (2007) Phase I clinical trial of STA-4783 with paclitaxel in patients with refractory solid tumors. *Clin Cancer Res* 13: 584-590

Kirshner J R, He S, Balasubramanyam V, Kepros J, Yang C Y, Zhang M, Du Z, Barsoum J, Bertin J (2008) Elesclomol induces cancer cell apoptosis through oxidative stress. *Mol Cancer Ther* 7: 2319-2327

Sheng-Tanner X, Bump E A, Hedley D W (1998) An oxidative stress-mediated death pathway in irradiated human leukemia cells mapped using multilaser flow cytometry. *Radiat Res* 150: 636-647

Hedley D W, McCulloch E A, Minden M D, Chow S, Curtis J (1998) Antileukemic action of buthionine sulfoximine: evidence for an intrinsic death mechanism based on oxidative stress. *Leukemia* 12: 1545-1552

Backway K L, McCulloch E A, Chow S, Hedley D W (1997) Relationships between the mitochondrial permeability transition and oxidative stress during ara-C toxicity. *Cancer Res* 57: 2446-2451

Hedley D W, Chow S (1994) Evaluation of methods for measuring cellular glutathione content using flow cytometry. *Cytometry* 15: 349-358

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating cancer in a patient comprising administering to the subject an effective amount of

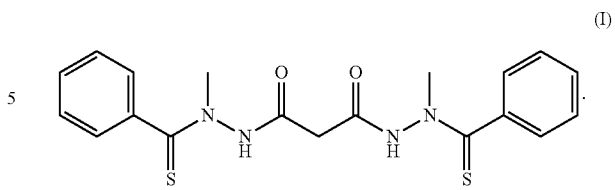

a salt, or a deprotonated form thereof complexed to a transition metal cation; or a compound represented by the following structural formula:

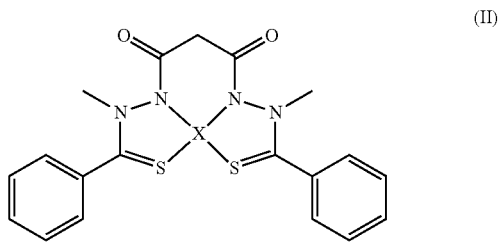

wherein X is a transition metal cation with a +2 charge; and an effective amount of an LDH inhibitor, wherein the subject has lactate dehydrogenase levels (LDH)≥0.8 ULN (upper limit of normal value).

2. The method of claim 1, wherein the patient has been diagnosed as being at risk of having cancer cells with elevated lactate dehydrogenase levels.

3. A method of treating cancer in a patient determined to have normal to low lactate dehydrogenase levels, comprising administering to the subject an effective amount of

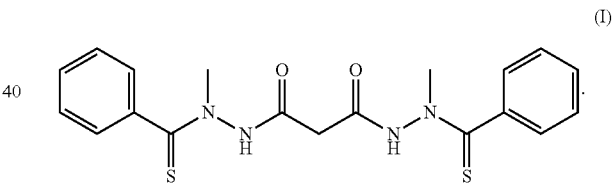

a salt, or a deprotonated form thereof complexed to a transition metal cation; or a compound represented by the following structural formula:

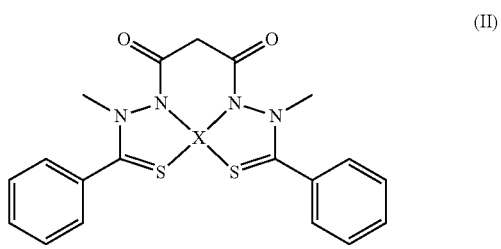

wherein X is a transition metal cation with a +2 charge, wherein the subject has lactate dehydrogenase levels (LDH)≤0.8 ULN (upper limit of normal value).

4. The method of claim 1, wherein the LDH inhibitor is oxamic acid or a salt thereof.

5. The method of claim 1, wherein the LDH inhibitor inhibits LDH-A.

6. A method of treating a patient for cancer, comprising determining the lactate dehydrogenase level in the patient; comparing the lactate dehydrogenase level to an upper limit of normal value (ULN); determining whether the lactate dehydrogenase level is over 0.8 ULN; and administering to the subject an effective amount of

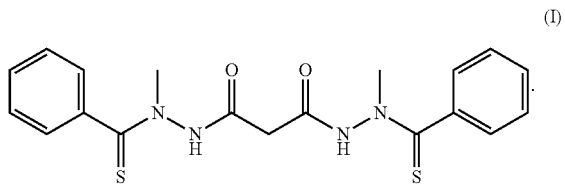 [SMILES: CN(NC(=O)CC(=O)NN(C)C(=S)c1ccccc1)C(=S)c1ccccc1]
(I)

a salt, or a deprotonated form thereof complexed to a transition metal cation; or a compound represented by the following structural formula:

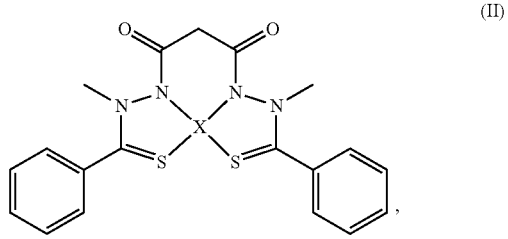
(II)

wherein X is a transition metal cation with a +2 charge; provided that if the lactate dehydrogenase level is above 0.8 ULN, an effective amount of an LDH inhibitor is also administered to the patient.

7. The method of claim 1, wherein the cancer is selected from the group consisting of renal cancer, skin cancer, bone marrow cancer, blood cell cancer, prostate cancer, ovarian cancer, and breast cancer.

8. The method of claim 7, wherein the blood cell cancer is leukemia, lymphoma or myeloma.

9. The method of claim 8, wherein the leukemia is selected from the group consisting of acute lymphocytic leukemia, acute myelocytic leukemia, chronic leukemia, polycythemia vera, lymphocytic leukemia, large granular lymphocytic leukemia, lymphoblastic leukemia, T-cell leukemia, T-lymphocytic leukemia, T-lymphoblastic leukemia, B cell leukemia, B-lymphocytic leukemia, B and T cell leukemia, B and T lymphocytic leukemia, myeloid leukemias, neutrophilic leukemia, eosinophilic leukemia, monocytic leukemia, myelomonocytic leukemia, Naegeli-type myeloid leukemia, and nonlymphocytic leukemia.

10. The method of claim 8, wherein the lymphoma is selected from the group consisting of Hodgkin's and non-Hodgkin's disease, and Waldenström macroglobulinemia.

11. The method of claim 1, wherein the compound is co-administered with an anti-cancer agent that stabilizes microtubules.

12. The method of claim 1, wherein the compound is co-administered with paclitaxel, docetaxel or analogs thereof.

13. The method of claim 1, wherein X is $Ni^{2+}$, $Cu^{2+}$, $Co^{2+}$, $Fe^{2+}$, $Zn^{2+}$, $Pt^{2+}$ or $Pd^{2+}$.

14. The method of claim 1, wherein X is $Cu^{2+}$.

15. The method of claim 1, wherein X is $Ni^{2+}$.

16. The method of claim 1, wherein the molar ratio of compound (I), a salt, or deprotonated form thereof to transition metal cation is equal to or greater than 0.5 and equal to or less than 2.0.

* * * * *